United States Patent [19]

Darms et al.

[11] 4,210,588
[45] Jul. 1, 1980

[54] SILICON-MODIFIED IMIDYL-PHTHALIC ACID DERIVATIVES

[75] Inventors: Roland Darms, Therwil; Siegfried Wyler, Dornach, both of Switzerland; Gerd Greber, Bad Vöslau, Austria

[73] Assignee: Ciba-Ceigy Corporation, Ardsely, N.Y.

[21] Appl. No.: 938,169

[22] Filed: Aug. 30, 1978

[30] Foreign Application Priority Data

Sep. 9, 1977 [CH] Switzerland .................. 11068/77

[51] Int. Cl.² .............. C07D 209/08; C07D 209/96; C09J 1/00
[52] U.S. Cl. .................. 260/326 E; 156/327; 156/330; 156/331; 156/333
[58] Field of Search .................. 260/326 E, 326.41

[56] References Cited

U.S. PATENT DOCUMENTS

| | | | |
|---|---|---|---|
| 3,414,584 | 12/1968 | Fink | 260/326 E |
| 3,478,074 | 11/1969 | Omietanski et al. | 260/326 E |
| 3,576,031 | 4/1971 | Holub et al. | 260/326 E |
| 3,901,913 | 8/1975 | Kim | 260/326 E |
| 3,966,531 | 6/1976 | Bargain | 260/326 E |
| 4,098,796 | 7/1978 | Guddal | 260/326 E |
| 4,107,174 | 8/1978 | Baumann et al. | 260/326.41 |

*Primary Examiner*—Anton H. Sutto
*Assistant Examiner*—M. C. Eakin
*Attorney, Agent, or Firm*—Joseph F. DiPrima

[57] ABSTRACT

The compounds according to the invention are Si-modified imidyl-phthalic acid derivatives of the formula

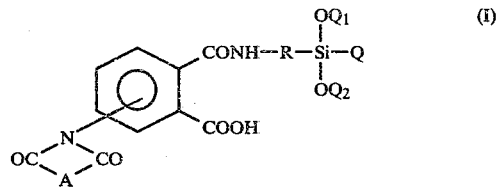

and the corresponding cyclized imide derivatives; in the formula, A is a radical which completes to a substituted or unsubstituted imidyl group, R is a divalent organic radical, $R_1$ and $R_2$ are each hydrogen or a monovalent organic radical and Q, $Q_1$ and $Q_2$ are each a monovalent organic radical. A typical example is 3-dimethyl-maleimidyl-phthalic acid N-(di-n-propoxymethylsilyl)-propylimide, which is obtained by reacting 3-dimethyl-maleimidyl-phthalic acid N-allylimide and di-n-propoxymethylsilane in solution, followed by cyclization. The products are used as adhesion promoters, for example between inorganic solids and organic resins.

4 Claims, No Drawings

SILICON-MODIFIED IMIDYL-PHTHALIC ACID DERIVATIVES

The present invention relates to novel silicon-modified imidyl-phthalic acid derivatives, processes for their preparation, and their use as adhesion promoters, for example between inorganic solids and organic resins.

German Offenlegungsschrift No. 2,020,842 has already disclosed unsaturated, imido-substituted organosilane compounds in which the imido group is bonded to the Si atom via a divalent hydrocarbon radical which may or may not be halogen-substituted. These products may be used for modifying the surface of cellulose substrates and for the preparation of aliphatically unsaturated, imido-substituted organopolysiloxanes.

The literature further discloses that various silanes, for example vinyltrichlorosilane, vinyl-tris-(2-methoxyethoxy)-silane γ-aminopropyltriethoxysilane, may be used as adhesion promoters for various applications, for example for the production of glass-fibre reinforced plastics, for sealants, for lacquers and for adhesives [compare, for example, Defazet, 28, 207–211 (1974) and Kunststoffe, 55, 909–912 (1965)].

However, the properties of the products obtained using these known adhesion promoters in part leave something to be desired, especially in respect of water absorption, resistance to thermal oxidation and/or dielectric properties.

It is the object of the present invention to provide novel adhesion promoters by means of which the above disadvantages may be avoided.

The novel silicon-modified imidyl-phthalic acid derivatives correspond to the formula I

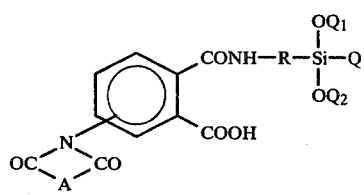

in which A is a radical of the formula

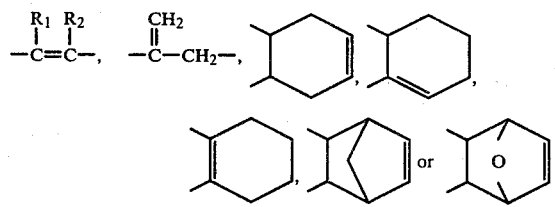

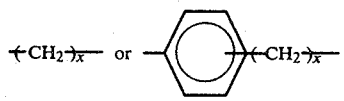

$R_1$ and $R_2$ independently of one another are hydrogen or methyl, Q is methyl, phenyl or $-OQ_3$, $Q_1$, $Q_2$ and $Q_3$ independently of one another are alkyl with 1–6 C atoms or phenyl, R is

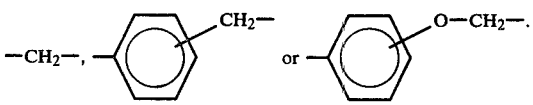

and, if A is a radical other than

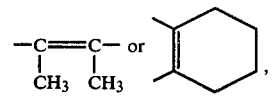

may also be

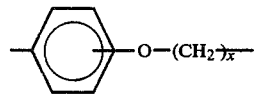

and x is an integer from 2 to 4.

The invention also relates to the derivatives which have been cyclised to give the corresponding imides.

The compounds of the formula I and the corresponding cyclised derivatives may be prepared by a method wherein a compound of the formula II

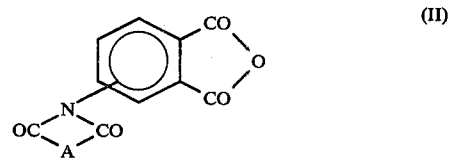

in which A is as defined under formula I, is reacted with an aminosilane of the formula III

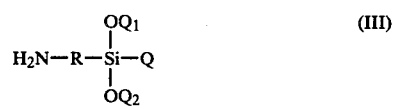

in which R, Q, $Q_1$ and $Q_2$ are as defined under formula I, after which the resulting amidocarboxylic acid may or may not be cyclised to the corresponding imide.

According to a modified process, compounds of the formula I which have been cyclised to the imide can also be prepared by a method wherein a compound of the formula IV

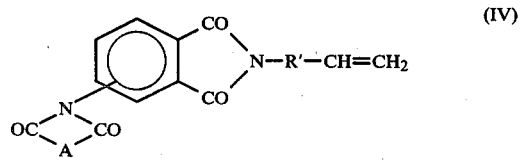

is reacted with a compound of the formula V

in which A, Q, $Q_1$ and $Q_2$ are as defined under formula II and R' is

The starting materials of the formula IV, in which A is

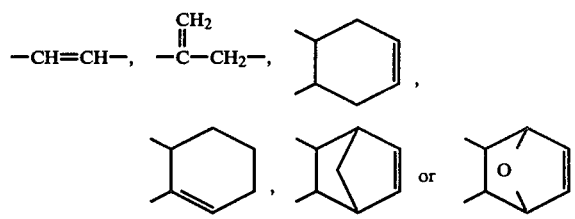

are novel and are also a subject of the present invention.

Alkyl groups $Q_1$, $Q_2$ and $Q_3$ may be straight-chain or branched, but the former is preferred. As examples of alkyl groups according to the definition there may be mentioned the methyl, ethyl, n-propyl, isopropyl, n-butyl, tert.-butyl, n-pentyl and n-hexyl group.

The imidyl groups

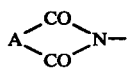

are preferably bonded to the benzene ring in the ortho-position to the —COOH or —CONH group. A is advantageously —CH═CH—,

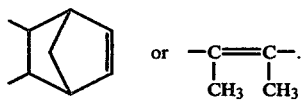

Preferred meanings of R are

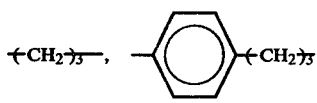

and, if A is a radical other than

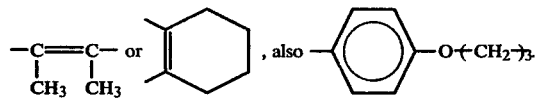

Preferred compounds of the formula I and preferred corresponding cyclised imide derivatives are those in which A is a radical

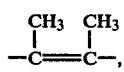

Q is methyl or alkoxy with 1-4 C atoms, $Q_1$ and $Q_2$ are each alkyl with 1-4 C atoms and R is ―(CH$_2$)$_3$―, or in which A is a radical

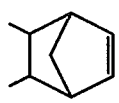

and especially —CH═CH—, Q is methyl or alkoxy with 1-4 C atoms, $Q_1$ and $Q_2$ are each alkyl with 1-4 C atoms and R is ―(CH$_2$)$_3$― and especially

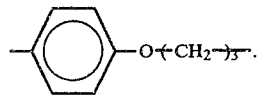

Particularly preferred compounds of the formula I, and corresponding cyclised imide derivatives, are those in which A and R have the abovementioned preferred meanings and Q is methyl, ethoxy or n-propoxy and $Q_1$ and $Q_2$ are n-propyl or ethyl.

The starting materials of the formula II are described in German Offenlegungsschrift No. 2,459,673. The aminosilanes of the formula III and the silanes of the formula V are also known. The compounds of the formula IV which may be used in the modified process of preparation, and which in some cases are novel compounds, may be prepared by reacting compounds of the formula II, in which A is

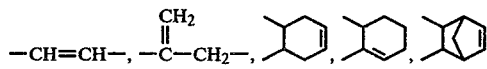

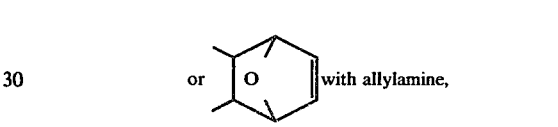

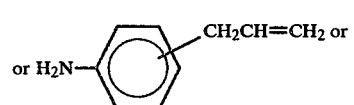

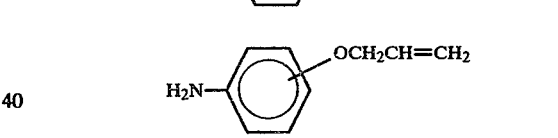

in the melt at temperatures of up to about 250° C. or in an aqueous-organic, or organic, medium at temperatures between about −15° C. and +150° C.

Examples of inert organic solvents suitable for the reaction in an aqueous-organic or organic medium are aromatic hydrocarbons, for example benzene, toluene and xylenes, cyclic ethers, for example tetrahydrofuran, tetrahydropyran and dioxane, N,N-dialkylamides of aliphatic monocarboxylic acids with 1-3 C atoms in the acid part, for example N,N-dimethylformamide, N,N-dimethylacetamide, N,N-diethylacetamide and N,N-dimethylmethoxyacetamide, cyclic amides, for example N-methyl-2-pyrrolidone, N-acetyl-2-pyrrolidone and N-methyl-ε-caprolactam, dialkyl ethers in which each alkyl part has 1-4 C atoms, for example diethyl ether and di-n-butyl ether, and dialkylsulphoxides, for example dimethyl-sulphoxide and diethylsulphoxide, The reaction of the phthalic anhydrides of the formula II with the aminosilanes of the formula III is advantageously carried out in an anhydrous organic solvent at temperatures between about −20° C. and +50° C., especially between about −15° C. and +25° C.

Suitable organic solvents are cyclic ethers, N,N-dialkylamides of aliphatic monocarboxylic acids, cyclic amides, dialkyl ethers and dialkyl-sulphoxides of the abovementioned type, as well as aliphatic and cycloaliphatic ketones, for example acetone, methyl ethyl ketone, cyclopentanone and cyclohexanone, hexamethylphosphorotriamide (hexametapol), N,N,N',N'-tetramethylurea and tetrahydrothiophene dioxide (sulfolane).

The reaction can also be carried out in mixtures of such solvents. On the other hand, it is also possible to dilute these preferred solvent systems with other organic solvents, for example aromatic, cycloaliphatic or aliphatic, chlorinated or non-chlorinated, hydrocarbons, for instance benzene, toluene, xylenes, cyclohexane, n-pentane, n-hexane, petroleum ether and methylene chloride.

The compounds of the formulae II and III are employed in approximately the stoichiometric amount. Advantageously, a slight excess of the aminosilane of the formula III, for example approximately 5–20% molar excess, is used. Aminosilanes of the formula III, in which

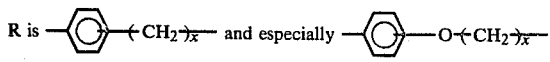

are particularly suitable for the reaction with anhydrides of the formula II.

The optional cyclisation of the amidocarboxylic acids, obtained from the above reaction, to give the corresponding imides may be carried out chemically or thermally, by methods known per se. Chemical cyclisation is advantageously effected by treatment with a dehydrating agent, used by itself or as a mixture with a tertiary amine. Examples of suitable dehydrating agents are acetic anhydride, propionic anhydride and dicyclohexylcarbodiimide, or mixtures of acetic anhydride and triethylamine.

The thermal cyclisation is effected by heating to temperatures of about 50°–250° C., preferably about 100°–150° C., with or without addition of an inert organic solvent and/or of an azeotropic entraining agent, for example xylenes or toluene. However, in some cases cyclisation of the amidocarboxylic acids obtained is superfluous, if these acids can be applied in the form of solutions as obtained from the reaction.

The reaction of compounds of the formula IV with silanes of the formula V by the modified process directly leads to imides and is advantageously also carried out in an inert organic solvent and in the presence of a catalyst.

Examples of catalysts which may be used are organic peroxides, for instance tert.-butyl hydroperoxide, di-tert.-butyl peroxide, benzoyl peroxide, diacyl peroxides and cumene hydroperoxide, and platinum and palladium catalysts, for instance platinum/charcoal catalysts or $PtCl_6H_2$ catalysts.

Examples of suitable inert organic solvents are aromatic hydrocarbons, for instance benzene, toluene and xylenes, cyclic ethers, for instance tetrahydrofuran, tetrahydropyran and dioxane, and ethylene glycol monoalkyl ethers and dialkyl ethers each with 1–4 C atoms in the alkyl portions, for instance ethylene glycol monomethyl ether, monoethyl ether, diethyl ether and di-n-butyl ether. Aromatic hydrocarbons are preferred. The reaction is advantageously carried out under a protective gas, for example nitrogen or argon.

The reaction temperatures are in general approximately between 80° and 150° C.; reaction temperatures between about 90° and 120° C. are preferred.

The compounds of the formula I are valuable adhesion promoters, especially between inorganic solids and organic resins, and may be used for a large number of applications in the adhesives industry and in the lacquer-using and plastics-processing industries.

The following are examples of some fields of use: improving the adhesion of special sealants, for example polysulphides, polyurethanes and polyacrylates, to various substrates, for example glass, aluminium and ceramics; encapsulating mineral fillers so as to improve the mechanical properties of the products prepared therewith, for example in the case of sand-filled masks and cores used in the foundry industry, mineral-filled cable mixtures or other mineral-filled plastics, for example filled thermosetting resins, for instance quartz-filled epoxide resins and filled unsaturated polyesters, filled thermoplastics, for instance polyamide-6,6 and polyethylene terephthalate, and filled elastomers, for instance natural rubber and synthetic rubber; and incorporation in adhesives, adhesive compositions and lacquers, for example adhesive compositions containing epoxide resins, and lacquers based on epoxides, polyacrylates, polyurethanes and vinyl chloride copolymers. However, the compounds mentioned are especially suitable for the manufacture of reinforced plastics, especially glass fibre-reinforced plastics, in particular composite materials, for instance laminates, in order to improve the adhesion between the substrate or matrix and the plastic applied thereto. The substrate per se may be in any desired form, for example in the form of fibres, fabrics or nonwovens, and preferably consists of glass or of mineral materials, for example quartz, mineral wool, asbestos, mica or metal fibres and foils. Examples of suitable plastics for the manufacture of such laminates are acrylates and polyester, epoxide, silicon, melamine, phenolic and furan resins, and also polyamides, polyamidoacids and polyimides, but especially polymers crosslinkable via C=C double bonds, for instance unsaturated polyesters, homopolymers and copolymers containing maleimidyl and nadicimidyl groups, their precursors or their mixtures with other polymers.

Relative to comparable composite materials which have been manufactured using known silicon-containing adhesion promoters, especially those of the type mentioned at the outset, glass fibre-reinforced composite materials manufactured using the adhesion promoters according to the invention, of the formula I, are distinguished especially by improved resistance to thermal oxidation, improved dielectric properties after exposure to moisture, and/or lower water absorption. The compounds of the formula I are also distinguished by good wetting of the substrates.

The adhesion promoters according to the invention are advantageously applied in the form of solutions in suitable organic solvents, for example N,N-dimethylformamide, N,N-dimethylacetamide, N-methyl-2-pyrrolidone, acetone, methyl ethyl ketone, tetrahydrofuran and dioxane, or in the form of dispersions or emulsions, in accordance with conventional techniques.

Preparation Examples

EXAMPLE 1

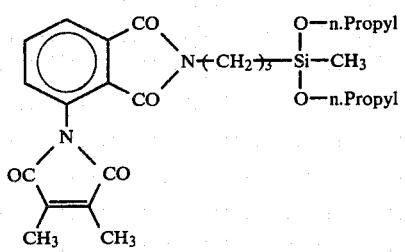

43.5 g (0.14 mol) of 3-dimethylmaleimidyl-phthalic acid N-allylimide and 0.5 ml ($1 \times 10^{-5}$ mol) of a solution of $H_2PtCl_6 \cdot 6 H_2O$ in propanol are heated, in 200 ml of anhydrous toluene, to 105° C. in a sulphonation flask, under a nitrogen atmosphere. A solution of 23 g (0.142 mol) of freshly distilled di-n-propoxymethylsilane in 100 ml of anhydrous toluene is added dropwise over a period of one hour, with stirring. The reaction mixture is then stirred for a further 3 hours at 105° C. After removing the solvent, the crude product obtained is distilled. 50 g (76% of theory) of 3-dimethylmaleimidyl-phthalic acid N-(di-n-propoxymethylsilyl)-propylimide are obtained in the form of a yellowish, very viscous oil; boiling point 225°–235° C./$10^{-3}$ mm Hg.

Analysis for $C_{24}H_{32}N_2O_6Si$ (molecular weight 472): Calculated: C, 60.99%; H, 6.82%; N, 5.93%; Si, 5.94%. Found: C, 61.0%; H, 6.9%; N, 6.1%; Si, 6.1%.

The 3-dimethylmaleimidyl-phthalic acid N-allylimide used in the above example may be prepared as follows:

54 g (0.2 mol) of 3-dimethylmaleimidyl-phthalic anhydride are dissolved in 200 ml of xylene at 50° C. A solution of 15 ml (0.2 mol) of allylamine is added dropwise. The reaction mixture is then heated under reflux for 5 hours, using a water separator. The solvent is removed in vacuo and the crude product is twice recrystallised from ethanol. 43.2 g (70% of theory) of 3-dimethylmaleimidyl-phthalic acid N-allylimide are obtained as white crystals of melting point 97°–100° C.

Analysis for $C_{17}H_{14}N_2O_4$ (molecular weight 310): calculated: C, 65.8%; H, 4.55%; N, 9.03%. found: C, 65.8%; H, 4.6%; N, 9.1%.

EXAMPLE 2

9.48 g (0.035 mol) of a 1:1 mixture of 3-dimethyl- and 4-dimethyl-maleimidyl-phthalic anhydride are dissolved in 140 ml of anhydrous N,N-dimethylacetamide in a sulphonation flask under nitrogen, and the solution is cooled to 0° C. A solution of 7.68 g (0.035 mol) of γ-aminopropyl-di-n-propoxy-methylsilane in 20 ml of N,N-dimethylacetamide is added dropwise, with stirring, and the reaction mixture is then stirred for a further 2 hours at 20°–25° C. A mixture of 3- and 4-dimethylmaleimidylphthalic acid mono-(di-n-propoxymethylsilyl)-propylamide, dissolved in N,N-dimethylacetamide, is obtained. This solution can be used for finishing glass fibres intended for the manufacture of glass fibre-reinforced composite materials.

The starting material 3-dimethylmaleimidylphthalic anhydride or the mixture of 3- and 4-dimethylmaleimidyl-phthalic anhydride can be prepared by the process described in German Offenlegungsschrift No. 2,459,673.

EXAMPLE 3

7.29 g (0.03 mol) of 4-maleimidyl-phthalic anhydride are dissolved in 125 ml of anhydrous N,N'-dimethylacetamide in a sulphonation flask under a $N_2$ atmosphere and the solution is cooled to 0° C. A solution of 8.86 g (0.03 mol) of 4-[γ-di-n-propoxymethyl-silyl]-propylaniline in 29 ml of N,N'-dimethylacetamide is added dropwise, with stirring, and the reaction mixture is then stirred for a further 2 hours at 20° to 25° C. The solution of the amidoacid formed can be used for finishing glass fibres intended for the manufacture of glass fibre-reinforced composite materials.

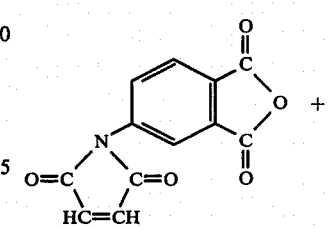

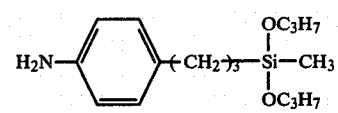

EXAMPLE 4

9.27 g (0.03 mol) of 3-nadic-imidyl-phthalic anhydride are dissolved in 125 ml of anhydrous N,N'-dimethylacetamide in a sulphonation flask under a nitrogen atmosphere and the solution is cooled to 0° C. A solution of 6.63 g (0.03 mol) of γ-aminopropyl-triethoxysilane in 26 ml of N,N'-dimethylacetamide is added dropwise, with stirring, and the reaction mixture is then stirred for a further 2 hours at 20° to 25° C. The solution of the amidoacid formed can be used for finishing glass fibres intended for the manufacture of glass fibre-reinforced composite materials.

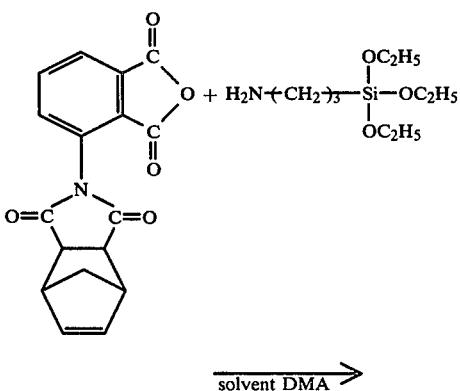

-continued

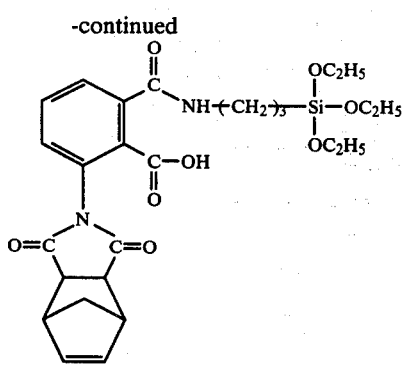

EXAMPLE 5

12.86 g (0.05 mol) of 3-itaconimidyl-phthalic anhydride are dissolved in 100 ml of anhydrous N,N'-dimethylacetamide in a sulphonation flask under a nitrogen atmosphere and the solution is cooled to 0° C. A solution of 14.77 g (0.05 mol) of 4-(γ-di-n-propoxymethylsilyl)-propyl-aniline in 15 ml of N,N'-dimethylacetamide is added dropwise, with stirring, and the reaction mixture is then stirred for a further 2 hours at 20° to 25° C. Thereafter, the amidoacid is thermally cyclised by heating to 120°–130° C., with addition of toluene as an azeotropic entraining agent; the corresponding 3-itaconimidyl-phthalic acid 4-(di-n-propoxymethylsilyl)-propylphenylimide is formed. After dilution with 140 ml of N,N'-dimethylacetamide, this solution can be used for finishing glass fibres intended for the manufacture of glass fibre-reinforced composite materials.

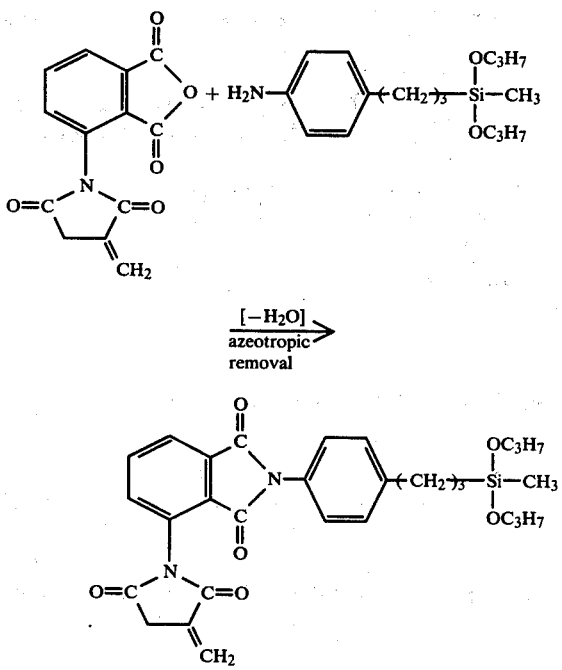

Use Example

(a) Impregnation of a Glass Fibre Fabric

A glass fibre fabric made from so-called E-glass, having a satin weave and weighing 280 g/m$^2$, is first thermally desized to about 0.1% by weight residual size content and is then impregnated with 2% solutions or emulsions of the adhesion promoters listed below. The adhesion promoter solutions are applied by immersion, with an impregnation speed of 0.5 m/minute, and the impregnated material is then dried for 20 minutes at 180° C. in a circulating air oven.

The prepregs obtained contain from 0.09 to 0.11% by weight, based on glass, of adhesion promoter.

The following are used as adhesion promoters (finishes):

(1) No adhesion promoter (2) Vinyltri-(2-methoxyethoxy)-silane ("Silan A 172" from Messrs. Union Carbide), 2% solution in N,N-dimethylformamide (DMF)

(3) γ-Aminopropyl-triethoxysilane ("Silan A 1100" from Messrs. Union Carbide), 2% solution in DMF (4) Adhesion promoter according to Preparation Example 1, 2% emulsion in DMF (5) Adhesion promoter solution according to Preparation Example 2, diluted with DMF to 2% by weight (6) Adhesion promoter according to Preparation Example 3, 2% solution in DMF (7) Adhesion promoter according to Preparation Example 4, 2% solution in DMF (8) Adhesion promoter according to Preparation Example 5, 2% solution in DMF

(b) Production of Copper-Covered Laminate Sheets 1.0 mol of N,N'-4,4'-diphenylmethane-bis-maleimide is dissolved in 500 g of furfuryl alcohol at 100° C. and the solution is cooled to 25° C. 0.4 mol of 4,4'-diaminodiphenylmethane is dissolved in 200 g of methyl glycol at 25° C. The two solutions are combined and mixed thoroughly. The glass fibre fabrics finished in accordance with section (a) are impregnated with this mixed solution by the immersion process at 25° C. and are then dried in a circulating air oven for 18 minutes at 180° C.; the resulting prepregs contain 29% by weight of resin. 10 layers of the impregnated fabric are then pressed hot between two 35 microns thick copper foils which have been pretreated by electrolytic surface coating with brass. The press is first kept under light contact pressure for 2 to 3 minutes; the pressure is then raised to 40 kp/cm$^2$ and the assembly is pressed for one hour at 180° C. The test specimens are then taken out of the press and post-cured for a further 6 hours in an oven at 240° C.; the resulting laminate sheets contain 35% by weight of resin.

Properties of the copper-covered laminate sheets obtained

Flexural strength in N/mm$^2$ according to ISO/R 178
  (a) Initial value
  (b) after 10 days' aging at 270° C.
Water absorption
  in % by weight, after 24 hours at 23° C. The measurements are carried out on flexural test specimens according to VSM Standard Specification 77,103.
Dielectric loss factor tg δ/50 c/s according to DIN 53,483
  (a) Initial value measured at 23° C.
  (b) after 6 hours' storage in boiling water
Dielectric constant ϵ$_r$/50 c/s according to DIN 53,483
  (a) Initial value measured at 23° C.
  (b) after 6 hours' storage in boiling water.
  ISO/R = International Standards Organisation /Recommendations
  VSM = Verein Schweizerischer Maschinenindustrieller DIN = Deutsche Industrie-Norm The results are summarised in Table I which follows. The numbering of the experimental products is the same as under (a).

Table I (Test values of the laminate sheets according to Use Example b)

| | Adhesion promoter - Product No. | | | | | | | |
|---|---|---|---|---|---|---|---|---|
| | 1 | 2 | 3 | 4 | 5 | 6 | 7 | 8 |
| Flexural strength, $N/mm^2$, initial value | 422.3 | 401 | 586.7 | 448.6 | 557.9 | 428.2 | 419.1 | 436.5 |
| After 10 days' aging at 270° C. | 284.4 | 108.8 | 162.8 | 313.4 | 326.7 | 289.8 | 286.7 | 304.1 |
| Water absorption in % by weight after 24 hours at 23° C. | 0.54 | 0.28 | 0.29 | 0.22 | 0.22 | 0.49 | — | — |
| Dielectric loss factor, $\delta$/50c/s, initial value | 1.08 | 1.15 | 2.71 | 0.29 | 0.29 | 0.23 | 0.25 | 0.25 |
| After 6 hours' storage in boiling water | 6.57 | 2.81 | 4.22 | 1.77 | 0.52 | 0.51 | 0.39 | 1.99 |
| Dielectric constant $\epsilon_r$/50 c/s, initial value | 5.1 | 5.4 | 5.1 | 5.4 | 5.5 | 5.2 | 5.0 | 5.1 |
| After 6 hours' storage in boiling water | 6.9 | 5.8 | 5.5 | 5.9 | 5.8 | 5.4 | 5.2 | 5.6 |

What is claimed is:

1. A compound of the formula I

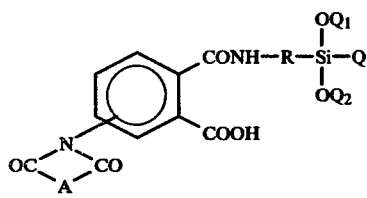

and its corresponding cyclised imide derivative, in which A is a radical of the formula

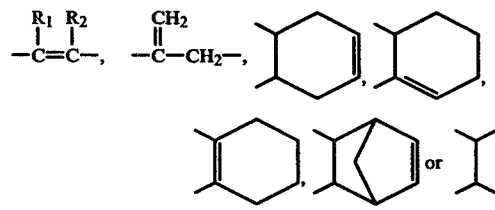

$R_1$ and $R_2$ independently of one another are hydrogen or methyl, Q is methyl, phenyl or —$OQ_3$, $Q_1$, $Q_2$ and $Q_3$ independently of one another are alkyl with 1–6 C atoms or phenyl, R is

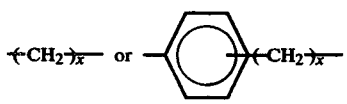

and, x is an integer from 2 to 4.

2. A compound of the formula I according to claim 1 and its corresponding cyclised imide derivative, in which A is a

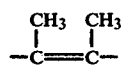

radical, Q is methyl or alkoxy with 1–4 C atoms, $Q_1$ and $Q_2$ are each alkyl with 1–4 C atoms and R is —$(CH_2)_3$—.

3. A compound of the formula I according to claim 1 and its corresponding cyclised imide derivative, in which A is a radical

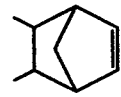

or —CH=CH—, Q is methyl or alkoxy with 1–4 C atoms, $Q_1$ and $Q_2$ are each alkyl with 1–4 C atoms and R is —$(CH_2)_3$—.

4. A compound of the formula I according to claim 1 and its corresponding cyclised imide derivative, in which A is the radical

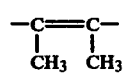

and R is —$(CH_2)_3$— or or A is a radical

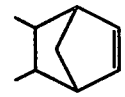

or —CH=CH— and R is —$(CH_2)_3$—, Q is methyl, ethoxy or n-propoxy and $Q_1$ and $Q_2$ are n-propyl or ethyl.

* * * * *